United States Patent [19]

Maurer et al.

[11] Patent Number: 5,043,337
[45] Date of Patent: Aug. 27, 1991

[54] INSECTICIDAL PYRIMIDIN-4-YL CARBAMATES

[75] Inventors: Fritz Maurer, Wuppertal; Kurt Findeisen, Odenthal; Jürgen Hartwig, Leverkusen, all of Fed. Rep. of Germany; Benedikt Becker, Bozen, Italy

[73] Assignee: Bayer Aktiengesellschaft, Leverkusen, Fed. Rep. of Germany

[21] Appl. No.: 504,465

[22] Filed: Apr. 4, 1990

[30] Foreign Application Priority Data

Apr. 8, 1989 [DE] Fed. Rep. of Germany ....... 3911488

[51] Int. Cl.$^5$ ................... A01N 43/54; C07D 403/12; C07D 413/12
[52] U.S. Cl. .............. 514/227.8; 514/228.2; 514/235.8; 514/234.5; 514/253; 514/252; 544/295; 544/122; 544/123; 544/58.4; 544/253; 544/116
[58] Field of Search ............. 514/252, 253, 234.5, 514/235.8, 227.8, 228.2; 544/122, 123, 58.4, 295, 253, 116

[56] References Cited

FOREIGN PATENT DOCUMENTS 0022511 1/1981 European Pat. Off. .
2838359 3/1980 Fed. Rep. of Germany .
1181657 2/1970 United Kingdom .

Primary Examiner—John M. Ford

Attorney, Agent, or Firm—Sprung Horn Kramer & Woods

[57] ABSTRACT

Insecticidal pyrimidin-4-yl carbamates of the formula

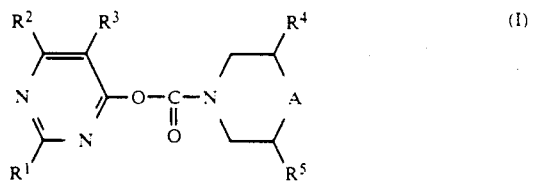

in which
$R^1$ represents alkoxy, alkylthio, alkylthioalkyl, alkylsulphinylalkyl, alkylsulphonylalkyl or dialkylamino,
$R^2$ represents hydrogen or alkyl,
$R^3$ represents hydrogen, alkyl or alkoxy or
$R^2$ and $R^3$ together represent a double-linked alkanediyl radical,
$R^4$ represents hydrogen or alkyl,
$R^5$ represents hydrogen or alkyl and
A represents oxygen, sulphur or a radical

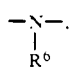

where $R^6$ represents alkyl.

12 Claims, No Drawings

INSECTICIDAL PYRIMIDIN-4-YL CARBAMATES

The invention relates to new pyrimidin-4-yl carbamates, to several processes for their preparation, and to their use as pesticides, in particular as insecticides.

It is known that certain pyrimidin-4-yl carbamates, such as, for example, 2-dimethylamino-5,6-diethylpyrimidin-4-yl dimethylcarbamate, have an insecticidal action (cf. GB-A 1,181,657). However, the action and duration of action of these compounds are not always entirely satisfactory, in particular at low application rates or when low concentrations of active compound are used.

There have now been found new pyrimidin-4-yl carbamates of the formula (I)

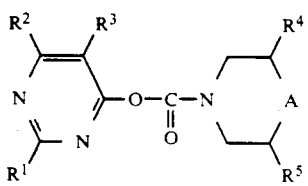

in which
$R^1$ represents alkoxy, alkylthio, alkylthioalkyl, alkylsulphinylalkyl, alkylsulphonylalkyl or dialkylamino,
$R^2$ represents hydrogen or alkyl,
$R^3$ represents hydrogen, alkyl or alkoxy or
$R^2$ and $R^3$ together represent a double-linked alkanediyl radical,
$R^4$ represents hydrogen or alkyl,
$R^5$ represents hydrogen or alkyl and
A represents oxygen, sulphur or a radical

where $R^6$ represents alkyl.

Furthermore, it has been found that the new pyrimidin-4-yl carbamates of the formula (I) are obtained when a) 4-hydroxy-pyrimidine derivatives of the formula (II)

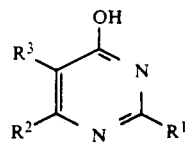

in which $R^1$, $R^2$ and $R^3$ have the abovementioned meanings, or the corresponding alkali metal salt, alkaline earth metal salt or ammonium salt, α) are reacted with carbamic acid chlorides of the formula (III)

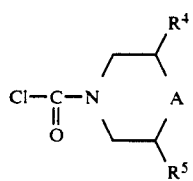

in which $R^4$, $R^5$ and A have the abovementioned meanings, if appropriate in the presence of an acid acceptor and, if appropriate, in the presence of a diluent, or (β) are reacted with phosgene, of the formula (IV)

$$COCl_2 \qquad (IV)$$

if appropriate in the presence of an acid acceptor and, if appropriate, in the presence of a diluent,
and the resulting pyrimidyl chloroformates of the formula (V)

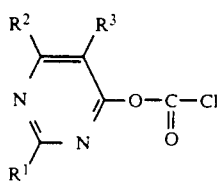

in which $R^1$, $R^2$ and $R^3$ have the abovementioned meanings, are isolated, if appropriate, and then reacted with amines of the general formula (VI)

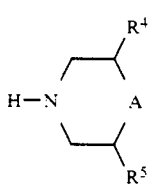

in which $R^4$, $R^5$ and A have the abovementioned meanings, if appropriate in the presence of an acid acceptor and if appropriate in the presence of a diluent, or b) the pyrimidin-4-yl carbamates which can be obtained by processes (a-α) and (a-β), of the formula

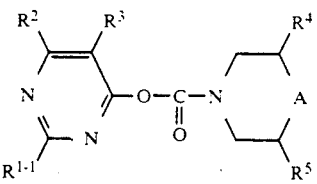

in which
$R^2$, $R^3$, $R^4$, $R^5$ and A have the abovementioned meanings and
$R^{1-1}$ represents alkylthioalkyl,
are reacted with an oxidant, if appropriate in the presence of diluents and, if appropriate, in the presence of a catalyst, and the compounds of the general formula (I) are isolated.

The new pyrimidin-4-yl carbamates of the formula (I) are distinguished in an outstanding manner by a particularly high activity as pesticides, in particular as insecticides.

The compounds of the formula (I) are furthermore distinguished by a particularly good systemic activity.

Preferred substituents or groups of the radicals listed in the formulae mentioned above and below are illustrated in the following:

Alkyl in the general formulae preferably denotes straight-chain or branched alkyl having 1 to 4 carbon atoms, in particular 1 or 2 carbon atoms: methyl, ethyl, n- and i-propyl and n-, i-, s- and t-butyl may be mentioned by way of example.

Unless defined otherwise, alkyl furthermore also preferably represents straight-chain or branched alkyl having 1 to 4, in particular 1 or 2, carbon atoms in alkyl-containing radicals, such as alkylsulphinylalkyl, dialkylamino, alkylsulphonylalkyl, alkoxy, alkylthio and alkylthioalkyl. The following may be mentioned by way of example: methyl, ethyl, n- and i-propyl, n-, i-, s- and t-butyl, methoxy, ethoxy, n- and i-propyloxy, methylthio, ethylthio, n- and i-propylthio, methylthiomethyl, ethylthiomethyl, 2-methylthioethyl, methylsulphinylmethyl, ethylsulphinylmethyl, 2-methylsulphinylethyl, methylsulphonylmethyl, ethylsulphonylmethyl, 2-methylsulphonylethyl, dimethylamino or diethylamino.

Preferred compounds from amongst the pyrimidin-4-yl carbamates of the formula (I) according to the invention are those in which $R^1$ represents alkoxy having 1 to 4 carbon atoms, alkylthio having 1 to 4 carbon atoms, alkylthioalkyl having 1 to 4 carbon atoms in the individual alkyl moieties, alkylsulphinylalkyl having 1 to 4 carbon atoms in the individual alkyl moieties, alkylsulphonylalkyl having 1 to 4 carbon atoms in the individual alkyl moieties and dialkylamino having 1 to 3 carbon atoms in the individual alkyl moieties, $R^2$ represents hydrogen or alkyl having 1 to 4 carbon atoms, $R^3$ represents hydrogen, alkyl having 1 to 4 carbon atoms or alkoxy having 1 to 4 carbon atoms or $R^2$ and $R^3$ together represent a double-linked, straight-chain or branched alkanediyl radical having 2 to 5 carbon atoms, $R^4$ represents hydrogen or alkyl having 1 to 3 carbon atoms, $R^5$ represents hydrogen or alkyl having 1 to 3 carbon atoms and A represents oxygen, sulphur or a radical $$-\underset{\underset{R^6}{|}}{N}-$$

where $R^6$ represents alkyl having 1 to 3 carbon atoms. Particularly preferred compounds of the formula (I) are those in which $R^1$ represents methoxy, ethoxy, methylthio, ethylthio, methylthiomethyl, ethylthiomethyl, 2-methylthioethyl, methylsulphinylmethyl, ethylsulphinylmethyl, 2-methylsulphinylethyl, methylsulphonylmethyl, ethylsulphonylmethyl, 2-methylsulphonylethyl, dimethylamino or diethylamino, $R^2$ represents hydrogen, methyl or ethyl, $R^3$ represents hydrogen, methyl, ethyl, isopropyl, methoxy or ethoxy or $R^2$ and $R^3$ together represent a double-linked alkanediyl radical having 3 or 4 carbon atoms, $R^4$ represents hydrogen or methyl, $R^5$ represents hydrogen or methyl and A represents oxygen, sulphur or the radical $$-\underset{\underset{CH_3}{|}}{N}- \quad \text{or} \quad -\underset{\underset{C_2H_5}{|}}{N}-$$

In addition to the compounds mentioned in the Preparation Examples, the pyrimidin-4-yl carbamates of the general formula (I) which are listed in Table 1 below may be mentioned individually:

TABLE 1

$$\text{(I)}$$

Structure with $R^2$, $R^3$ on the alkene; $R^4$, $R^5$, A on the ring; linked via $-O-C(=O)-N-$; $R^1$ on the pyrimidine N side.

| $R^1$ | $R^2$ | $R^3$ | $R^4$ | $R^5$ | A |
|---|---|---|---|---|---|
| $OCH_3$ | $CH_3$ | $CH_3$ | H | H | O |
| $SCH_3$ | $CH_3$ | $CH_3$ | H | H | O |
| $CH_2CH_2-SCH_3$ | H | $OCH_3$ | H | H | O |
| $CH_2CH_2-SO_2CH_3$ | H | $OCH_3$ | H | H | O |
| $CH_2CH_2-SCH_3$ | $CH_3$ | $CH_3$ | H | H | O |
| $CH_2CH_2-SO_2CH_3$ | $CH_3$ | $CH_3$ | H | H | O |
| $CH_2-SO_2-C_2H_5$ | $CH_3$ | $CH_3$ | H | H | O |
| $CH_2-SO_2-CH_3$ | $CH_3$ | $C_2H_5$ | H | H | O |
| $CH_2-SO_2-CH_3$ | $CH_3$ | $C_3H_7$-i | H | H | O |
| $CH_2-SO_2-CH_3$ | H | $C_3H_7$-i | H | H | O |
| $CH_2-SO_2-CH_3$ | H | $OC_2H_5$ | H | H | O |
| $CH_2-SO_2-CH_3$ | $-CH_2CH_2CH_2CH_2-$ | | H | H | O |
| $CH_2-SO_2-CH_3$ | $CH_3$ | $CH_3$ | H | H | O |
| $CH_2-SO-CH_3$ | $-CH_2-CH_2-CH_2-$ | | H | H | O |
| $N(CH_3)_2$ | $CH_3$ | $CH_3$ | $CH_3$ | $CH_3$ | O |
| $CH_2-SO_2-CH_3$ | $-CH_2-CH_2-CH_2-$ | | $CH_3$ | $CH_3$ | O |
| $CH_2CH_2SO_2CH_3$ | H | $C_3H_7$-n | H | H | O |

If, for example, 2-methylsulphonylmethyl-4-hydroxy-5-methoxypyrimidine and morpholinocarbamic acid chloride are used as starting substances, process (a-α) according to the invention can be outlined by the following equation:

[Reaction scheme showing 5-methoxy-2-(methylsulphonylmethyl)-4-hydroxypyrimidine + morpholine-4-carbonyl chloride → carbamate product, with "+ Base / − HCl"]

If, for example, 2-methylsulphonylmethyl-4-hydroxy-5,6-dimethylpyrimidine, phosgene and dimethylmorpholine are used as starting substances, process (a-β) according to the invention can be outlined by the following equation:

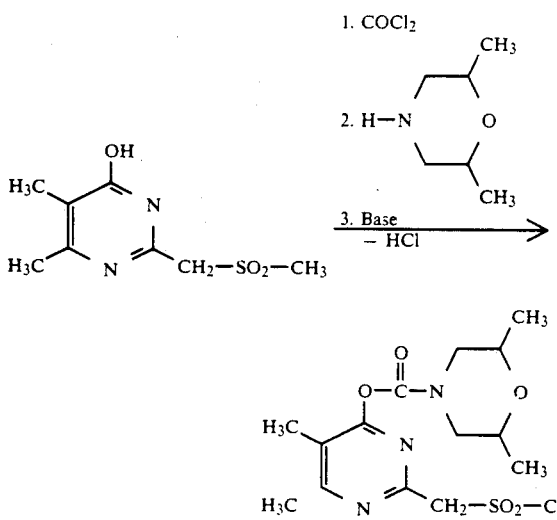

If, for example, O-(2-methylthiomethyl-5,6-dimethyl-pyrimidin-4-yl) morpholinocarbamate are used as the starting substances and hydrogen peroxide in the presence of catalytic amounts of ammonium molybdate is used as the oxidant, process (b) according to the invention can be outlined by the following equation:

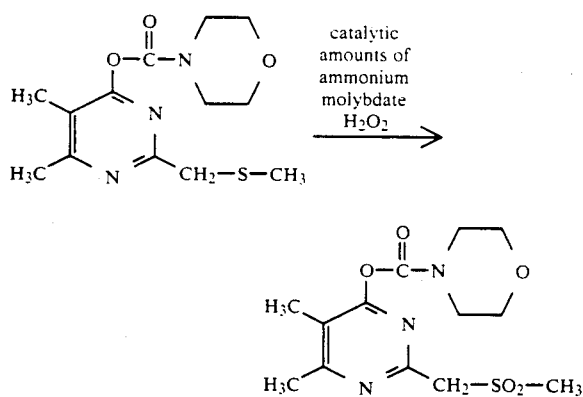

Formula (II) provides a definition of the 4-hydroxypyrimidine derivatives or the corresponding alkali metal salts, alkaline earth metal salts or ammonium salts to be employed as starting substances in processes (a-α) and (a-β) according to the invention for the preparation of the new pyrimidin-4-yl carbamates of the formula (I). In this formula, $R^1$, $R^2$ and $R^3$ represent those radicals which have been mentioned above in the definition in formula (I). Preferred salts which are employed as the alkali metal salts or alkaline earth metal salts are the sodium, potassium or calcium salts.

The compounds of the formula (II) are known and/or can be prepared by generally known processes and methods (cf., for example, DE-A 3,445,465 and DE-A 3,324,399).

Formula (III) provides a definition of the carbamic acid chlorides furthermore to be employed as starting substances in process (a-α) according to the invention. In this formula, $R^4$, $R^5$ and A represent those radicals which have been indicated in the definition in formula (I).

The compounds of the formula (III) are known and/or can be obtained by known methods (cf. DE-A 2,360,362, DE-A 1,961,176, EP-A 180,115, Chemical Abstracts 1953, 12,302 and Chemical Abstracts 1957, 434).

Phosgene, which is furthermore to be employed as a starting substance in process (a-α) according to the invention, is a generally known compound of organic chemistry.

Formula (VI) provides a definition of the amines furthermore to be employed as starting substances in process (a-β) according to the invention. In this formula, $R^4$, $R^5$ and A represent those radicals which have been indicated in the definition in formula (I).

The compounds of the formula (VI) are generally known compounds of organic chemistry.

Formula (Ia) provides a definition of the pyrimidin-4-yl caramates to be employed as starting substances in process (b) according to the invention. In this formula, $R^{1-1}$, $R^2$, $R^3$, $R^4$, $R^5$ and A represent those radicals which have been indicated in the definition in formula (I).

The compounds of the formula (Ia) are new and the subject of the invention. They can be obtained by processes (a-α) and (a-β).

Processes (a-α) and (A-β) according to the invention for the preparation of the new compounds of the formula (I) are preferably carried out using diluents and acid acceptors.

Diluents which are suitable for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

Acid acceptors which can be employed in the processes according to the invention are all acid-binding agents which can customarily be used for reactions of this type. The following are preferably suitable: alkaline earth metal hydroxides, such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

In processes (a-α) and (a-β) according to the invention, the reaction temperatures can be varied within a substantial range. In general, the processes are carried out at temperatures between 0° C. and 100° C., preferably at temperatures between 10° C. and 80° C.

Processes (a-α) and (a-β) according to the invention are generally carried out under atmospheric pressure. However, it is also possible to carry out the processes under increased or reduced pressure.

For carrying out processes (a-α) and (a-β) according to the invention, the starting substances are generally employed in approximately equimolar amounts. However, an excess of one or the other component of up to about 10% does not create any problems.

In general, the reactants are combined in one of the abovementioned solvents, and the mixture is stirred for several hours, the temperature being maintained within the range indicated above.

To work up the mixture, which is carried out by customary methods, it is concentrated, water is added to the residue, and the product which crystallizes out is filtered off with suction, washed and dried.

Process (b) according to the invention is preferably carried out in the presence of water as a diluent and in the presence of catalytic amounts of molybdenum salts, such as, for example, ammonium molybdate.

In general, process (b) according to the invention is carried out at temperatures between −20° C. and +100° C. The temperature range within 0° C. and 80° C. is preferred, in particular within 20° C. and 60° C. In general, the reactions are carried out under atmospheric pressure.

To carry out process (b) according to the invention, 1 to 3.5 moles, preferably 1.5 to 3.0 moles, in particular 2.0 to 2.8 moles, of hydrogen peroxide are added dropwise and, if appropriate, with cooling to a mixture of 1 mole of 2-alkylthio-alkylene-pyrimidin-4-yl carbamate, 0.01 to 10.0 g, preferably 0.05 to 5.0 g, in particular 0.1 to 2.0 g, of ammonium molybdate, and 10 to 500 ml, preferably 20 to 300 ml, in particular 50 to 200 ml of water. When the reaction ceases to proceed, the solids are filtered off with suction, washed and dried.

The compounds of the formula (I) are usually obtained in solid form and can be purified by recrystallization. They are characterized by the melting point.

The active compounds are suitable for controlling animal pests, preferably arthropods, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella.* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus. Gibbium psylloides,* Tribolium spp., *Tenebrio molitor,* Agriotes spp., Cono derus spp., *Melolontha melolontha. Amphimallon solsti tialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp. Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds of the formula (I) according to the invention are distinguished by an excellent insecticidal activity. In particular when employed as soil insecticides, they show an excellent action against aphids, such as, for example, Myzus persicae and Aphis fabae. Furthermore, the compounds of the formula (I) are distinguished by a particularly good systemic and root-systemic activity.

Thus, the new compounds are particularly highly suitable for use in the long-lasting control of soil insects.

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations in general contain between 0.1 and 95 per cent by weight of active compound, preferably between 0.5 and 90%.

The active compounds can le present in their commercially available formulations and in the use forms prepared from these formulations as a mixture with other active compounds, such as insecticides, attractants, sterilants, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms, etc.

Furthermore, the active compounds can be present in their commercially available formulations and in the use forms prepared from these formulations as a mixture with synergists. Synergists are compounds which increase the action of the active compounds, without it being necessary for the added synergist to be active itself.

The active compound content of the use forms prepared from the commercially available formulations can vary within wide limits. The active compound concentration of the use forms can be from 0.0000001 up to 95% by weight of active compound, preferably between 0.0001 and 1% by weight.

They are used in a manner designed to suit the use forms.

When used against hygiene pests and pests of stored products, the active compounds are distinguished by an excellent residual action on wood and clay and by a good stability to alkalis on limed substrates.

The preparation and the use of the active compounds according to the invention can be seen from the examples which follow.

PREPARATION EXAMPLES

Example 1

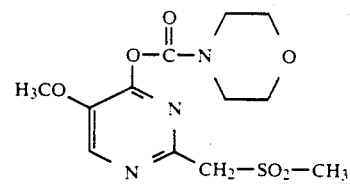

Process (a-α)

15 g (0.1 mol) of morpholinocarbamic acid chloride are added to a mixture of 21.8 g (0.1 mol) of 2-methylsulphonyl-4-hydroxy-5-methoxypyrimidine, 16.6 g (0.12 mol) of potassium carbonate, 0.6 g of diazabicyclooctane and 200 ml of acetone. The reaction mixture is stirred for 18 hours at 40° C., the solvent is then distilled off under reduced pressure, and the residue is stirred with 100 ml of water. The product which has precipitated is filtered off with suction, which gives 12.5 g (38% of theory) of O-(2-methylsulphonylmethyl-5-methoxy-pyrimidin-4-yl) morpholinocarbamate in the form of white crystals of melting point 138° C.

Example 2

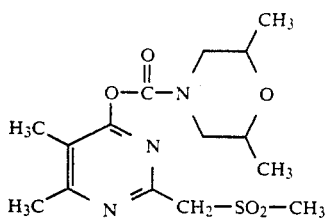

Process (a-β)

A solution of 11 g (0.06 mol) of 2-methylsulphonyl-methyl-4-hydroxy-5,6-dimethylpyrimidine and 8.6 ml (0.062 mol) of triethylamine in 200 ml of acetonitrile is added dropwise at −8° C. to −3° C. to 30 g of a 20% strength solution of phosgene in toluene. Stirring of the reaction mixture is continued for 1 hour at −5° C. to 0° C., and a mixture of 6.9 g (0.06 mol) of 2,6-dimethyl-morpholine and 9.6 g (0.07 mol) of triethylamine are then added at 0° to 10° C. Stirring of the reaction solution is continued for 18 hours at room temperature, the solvent is evaporated under reduced pressure, 200 ml of water are added, and the mixture is extracted twice, using 150 ml of methylene chloride each time. The organic phases are dried over sodium sulphate and evaporated under reduced pressure. The residue is triturated with 50 ml of petroleum ether, and the product crystallizes out and is then filtered off with suction.

This gives 14.3 g (67% of theory) of O-(2-methylsulphonylmethyl-5,6-dimethylpyrimidin-4-yl) 2,6-dimethylmorpholinocarbamate in the form of colorless crystals of melting point 103° C.

Example 3

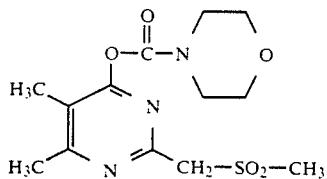

Process (b)

8.5 g (0.075 mol) of 3(% strength hydrogen peroxide is added to a mixture of 8.9 g (0.03 mol) of O-(2-methyl-thiomethyl-5,6-dimethyl-pyrimidin-4-yl) morpholinocarbamate, 50 ml of water and 0.1 g of ammonium molybdate, and the mixture is stirred for 18 hours. The product which has precipitated is then filtered off with suction, washed with 50 ml of ice-water and dried in the air.

This gives 6.3 g (64% of theory) of O-(2-methylsulphonylmethyl-5,6-dimethyl-pyrimidin-4-yl morpholinocarbamate in the form of colorless crystals of melting point 147° C.

The end products of the formula (I)

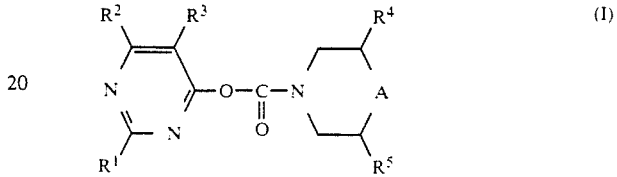

which are listed in Table 2 below are obtained analogously to Examples 1 to 3 and with consideration of the instructions in the description of the processes according to the invention:

TABLE 2

| Example No. | $R^1$ | $R^2$ | $R^3$ | $R^4$ | $R^5$ | A | Melting point [°C.]/ Refractive index |
|---|---|---|---|---|---|---|---|
| 4 | $CH_2SO_2CH_3$ | —$CH_2CH_2CH_2$— | | H | H | O | 144 |
| 5 | $CH_2SCH_3$ | H | $OCH_3$ | H | H | O | 51 |
| 6 | $CH_2SCH_3$ | $CH_3$ | $CH_3$ | H | H | O | 54 |
| 7 | $N(CH_3)_2$ | $CH_3$ | $CH_3$ | H | H | O | 82 |
| 8 | $CH_2SCH_3$ | —$CH_2CH_2CH_2$— | | H | H | O | 108 |
| 9 | $CH_2SO_2CH_3$ | $CH_3$ | $CH_3$ | H | H | S | 138 |
| 10 | $CH_2SO_2CH_3$ | $CH_3$ | $CH_3$ | H | H | $N-CH_3$ | 101 |
| 11 | $CH_2SO_2CH_3$ | H | $CH_3$ | H | H | O | 122 |
| 12 | $CH_2CH_2SCH_3$ | H | $CH_3$ | H | H | O | $n_D^{20}$ 1.5462 |
| 13 | $CH_2CH_2SO_2$ $\vert$ $CH_3$ | H | $CH_3$ | H | H | O | 106 |
| 14 | $N(CH_3)_2$ | —$CH_2CH_2CH_2$— | | H | H | O | 104 |
| 15 | $CH_2SCH_3$ | H | $C_3H_7$-i | H | H | O | $n_D^{24}$ 1.5441 |
| 16 | $CH_2SO_2CH_3$ | H | $C_3H_7$-i | H | H | O | 118 |

USE EXAMPLES

In the Use Examples below, the compound below was used as comparison substance:

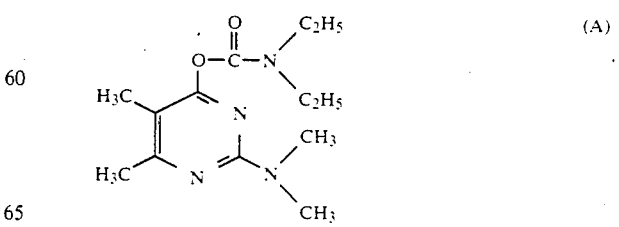

2-dimethylamino-5,6-dimethylpyrimidin-4-yl dimethylcarbamate (known from GB-A 1,181,657)

Example A

Myzus test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*), which are heavily infested with the peach aphid (*Myzus persicae*) are treated by being dipped into the active compound preparation of the desired concentration.

After the specified period cf time, the destruction in % is determined. 100% means that all the aphids have been killed; 0% means that none of the aphids have been killed.

In this test, for example, the following compounds of Preparation Examples (1), (3), (4), (5), (6), (7) and (8) showed a degree of destruction of 85 to 100% after 1 day, compared with 10% of the comparison compound (A).

Example B

Aphis test (systemic action)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Bean plants (*Vicia faba*) which are heavily infested with the black bean aphid (*Aphis fabae*) are each watered with 20 ml of the preparation of the active compound of the desired concentration in such a way that the preparation of the active compound penetrates into the soil without wetting the shoot. The active compound is taken up by the roots and passes to the shoot.

After the desired period of time, the destruction in % is determined. 100% means that all the aphids have been killed; 0% means that none of the aphids have been killed.

In this test, for example, the following compounds of Preparation Examples (3), (4), (5), (6), (7) and (8) show a degree of destruction of 95 to 100% after 4 days compared with 20% of the comparison compound (A).

Example C

Critical concentration test/root systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically, no importance here, only the amount by weight of active compound per unit volume of soil, which is given in ppm (=mg/l), being decisive. The treated soil is transferred into pots which are then planted with cabbage (*Brassica oleracea*). Thus, the active compound can be taken up by the plant roots from the soil and passed to the leaves.

To demonstrate the root-systemic effect, the above-mentioned test insects are placed after 7 days exclusively on the leaves. After a further 2 days, the evaluation is carried out by counting or estimating the dead insects. The destruction figures are used for calculating the root-systemic action of the active compound. It is 100% if all the test insects have been destroyed and 0% if just as many test insects are still alive as in the untreated control.

In this test, for example, the compounds of Preparation Examples (1), (3), (4), (5), (6), (7), (8) (11), (12), (13), (14), (15) and 16) show a destruction of 100% at an exemplary active compound concentration of 10 ppm.

It is understood that the specification and examples are illustrative but not limitative of the present invention and that other embodiments within the spirit and scope of the invention will suggest themselves to those skilled in the art.

We claim:

1. A pyrimidin-4-yl carbamate of the formula

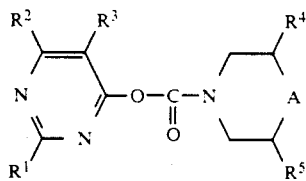

in which
R$^1$ represents alkoxy having 1 to 4 carbon atoms, alkylthio having 1 to 4 carbon atoms, alkylthioalkyl having 1 to 4 carbon atoms in the individual alkyl moieties, alkylsulphinylalkyl having 1 to 4 carbon atoms in the individual alkyl moieties, alkylsulphonylalkyl having 1 to 4 carbon atoms in the individual alkyl moieties and dialkylamino having 1 to 3 carbon atoms in the individual alkyl moieties,
R$^2$ represents hydrogen or alkyl having 1 to 4 carbon atoms, and
R$^3$ represents hydrogen, alkyl having 1 to 4 carbon atoms or alkoxy having 1 to 4 carbon atoms or
R$^2$ and R$^3$ together represent a double-linked, straight-chain or branched alkanediyl radical having 2 to 5 carbon atoms,
R$^4$ represents hydrogen or alkyl having 1 to 3 carbon atoms,
R$^5$ represents hydrogen or alkyl having 1 to 3 carbon atoms and
A represents oxygen, sulphur or a radical

where R$^6$ represents alkyl having 1 to 3 carbon atoms.

2. A pyrimidin-4-yl carbamate according to claim 1, in which

R¹ represents methoxy, ethoxy, methylthio, ethylthio, methylthiomethyl, ethylthiomethyl, 2-methylthioethyl, methylsulphinylmethyl, ethylsulphinylmethyl, 2-methylsulphinylethyl, methylsulphonylmethyl, ethylsulphonylmethyl, 2-methylsulphonylethyl, dimethylamino or diethylamino, R² represents hydrogen, methyl or ethyl, and R³ represents hydrogen, methyl, ethyl, isopropyl, methoxy or ethoxy or R² and R³ together represent a double-linked alkanediyl radical having 3 or 4 carbon atoms, R⁴ represents hydrogen or methyl, R⁵ represents hydrogen or methyl and A represents oxygen, sulphur or the radical

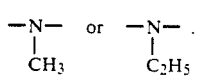

3. A compound according to claim 1, wherein such compound is O-(2-methylsulphonylmethyl-5-methoxy-pyrimidin-4-yl) morpholinocarbamate of the formula

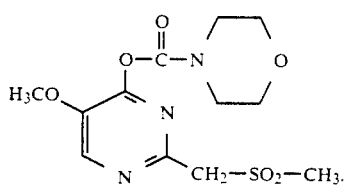

4. A compound according to claim 1, wherein such compound is O-(2-methylsulphonylmethyl-5,6-dimethyl-pyrimidin-4-yl) morpholinocarbamate of the formula

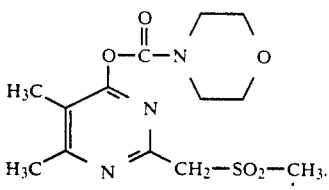

5. A compound according to claim 1, wherein such compound is O-(2-methylsulphonylmethyl-5,6-trimethylene-pyrimidin-4-yl) morpholinocarbamate of the formula

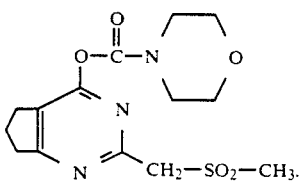

6. A compound according to claim 1, wherein such compound is O-(2-methylthiomethyl-5,-methoxy-pyrimidin-4-yl) morpholinocarbamate of the formula

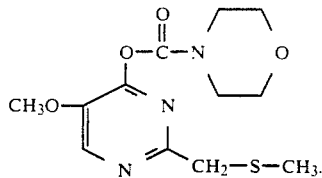

7. A compound according to claim 1, wherein such compound is O-(2-methylthiomethyl-5,6-dimethyl-pyrimidin-4-yl) morpholinocarbamate of the formula

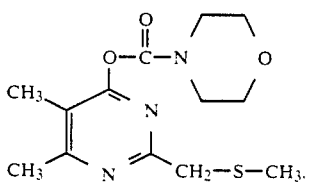

8. A compound according to claim 1, wherein such compound is O-(2-dimethylamino-5,6-dimethyl-pyrimidin-4-yl) morpholinocarbamate of the formula

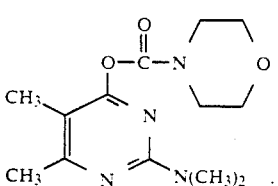

9. A compound according to claim 1, wherein such compound is O-(2-methylthiomethyl-5,6-trimethylene-pyrimidin-4-yl) morpholinocarbamate of the formula

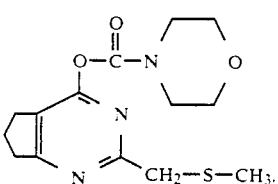

10. An insecticidal composition comprising an insecticidally effective amount of a compound according to claim 1, and a diluent.

11. A method of combating insects which comprises applying to such insects or to an insect habitat an insecticidally effective amount of a compound according to claim 1.

12. The method according to claim 11, wherein such compound is

O-(2-methylsulphonylmethyl-5,-methoxy-pyrimidin-4-yl) morpholinocarbamate,

O-(2-methylsulphonylmethyl-5,6-dimethyl-pyrimidin-4-yl) morpholinocarbamate,

O-(2-methylsulphonylmethyl-5,6-trimethylene-pyrimidin-4-yl) morpholinocarbamate, O-(2-methylthiomethyl-5,-methoxy-pyrimidin-4-yl) morpholinocarbamate, O-(2-methylthiomethyl-5,6-dimethyl-pyrimidin-4-yl) morpholinocarbamate, O-(2-dimethylamino-5,6-dimethyl-pyrimidin-4-yl) morpholinocarbamate or O-(2-methylthiomethyl-5,6-trimethylene-pyrimidin-4-yl) morpholinocarbamate.

* * * * *